(12) United States Patent
Sartorius et al.

(10) Patent No.: US 8,901,497 B2
(45) Date of Patent: Dec. 2, 2014

(54) METHOD FOR CREATING AND COHERENTLY DETECTING TERAHERTZ RADIATION

(75) Inventors: Bernd Sartorius, Berlin (DE);
Heinz-Gunter Bach, Berlin (DE);
Helmut Roehle, Berlin (DE)

(73) Assignee: Fraunhofer-Gesellschaft zur Förderung der angewandten Forschung e.V. (DE)

( * ) Notice: Subject to any disclaimer, the term of this patent is extended or adjusted under 35 U.S.C. 154(b) by 789 days.

(21) Appl. No.: 12/677,981

(22) PCT Filed: Sep. 12, 2008

(86) PCT No.: PCT/EP2008/007840
§ 371 (c)(1),
(2), (4) Date: Oct. 25, 2010

(87) PCT Pub. No.: WO2009/036984
PCT Pub. Date: Mar. 26, 2009

(65) Prior Publication Data
US 2011/0031400 A1    Feb. 10, 2011

(30) Foreign Application Priority Data
Sep. 14, 2007  (DE) .................... 10 2007 044 839

(51) Int. Cl.
*H01L 31/167*    (2006.01)
*G01N 21/35*    (2014.01)

(52) U.S. Cl.
CPC .................. *G01N 21/3581* (2013.01)
USPC ..................................... 250/338.4

(58) Field of Classification Search
USPC ..................................... 250/338.4
See application file for complete search history.

(56) References Cited

U.S. PATENT DOCUMENTS 5,687,261 A * 11/1997 Logan ............................ 385/24
5,789,750 A    8/1998 Nuss
5,952,818 A *  9/1999 Zhang et al. .................... 324/96

(Continued)

FOREIGN PATENT DOCUMENTS

| JP | 2006229156 A | 8/2006 |
|---|---|---|
| WO | WO-9828656 | 7/1998 |
| WO | WO-2006123162 A1 | 11/2006 |
| WO | WO-2006123163 A1 | 11/2006 |

OTHER PUBLICATIONS

Zimdars et al., A compact, Fiber-Pigtailed, Terahertz Time Domain Spectroscopy System, 2000).*

(Continued)

*Primary Examiner* — David Porta
*Assistant Examiner* — Djura Malevic
(74) *Attorney, Agent, or Firm* — Schwegman Lundberg & Woessner, P.A.

(57) ABSTRACT

The present invention relates to a device for creating and coherently detecting terahertz radiation, comprising a laser light source (1), a transmission antenna (2) that can be activated by the laser light source (1) for creating the terahertz radiation, and a receiver with a receiver antenna (3) that can be activated by the same laser light source (1), wherein the transmission antenna (2) comprises a photo diode as a light-sensitive element and the receiver antenna (3) a fast photoconductor as a light-sensitive element. The invention further relates to a use of such a device for analyzing a sample.

15 Claims, 2 Drawing Sheets

(56) References Cited

U.S. PATENT DOCUMENTS

Figure 1:
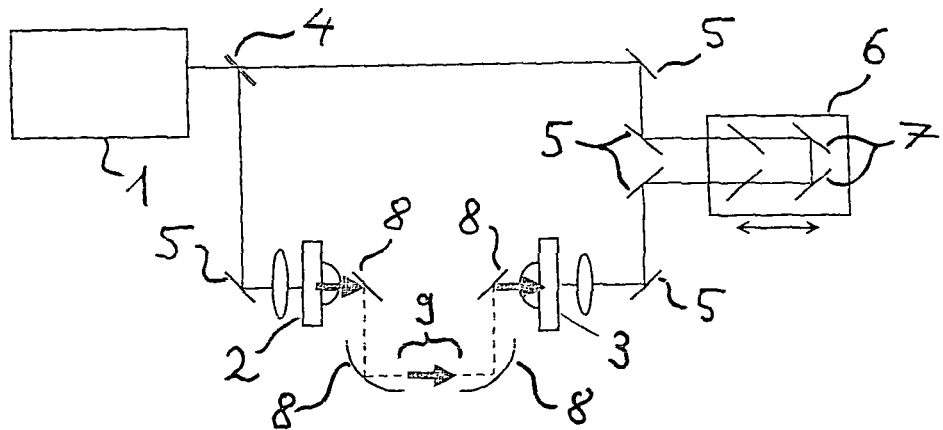

| | | | |
|---|---|---|---|
| 6,111,416 A * | 8/2000 | Zhang et al. | 324/244.1 |
| 2004/0166817 A1 * | 8/2004 | Mokhtari et al. | 455/91 |
| 2005/0100866 A1 | 5/2005 | Arnone et al. | |
| 2006/0273255 A1 * | 12/2006 | Volkov et al. | 250/336.1 |
| 2009/0135857 A1 * | 5/2009 | Oh et al. | 372/4 |

OTHER PUBLICATIONS

"European Application No. 08 802 360.1, European Search Report dated Jan. 20, 2011", (Jan. 20, 2011), 4 pgs.

Hirata, Akihiko, et al., "120-GHz-Band Millimeter-Wave Photonic Wireless Link for 10-Gb/s Data Transmission", IEE Transactions on Microwave Theory and Techniques, vol. 54, No. 5, (May 2006), 1937-1944.

"International Application Serial No. PCT/EP2008/007840, International Search Report and Written Opinion mailed Feb. 2, 2009", 17 pgs.

Dohler, G. H., et al., "THz-photomixer based on quasi-ballistic transport", *Semiconductor Science and Technology*, vol. 20, No. 7, (Jul. 1, 2005), S178-S190.

Dreyhaupt, A., et al., "High-intensity terahertz radiation from a microstructured large-area photoconductor", *Applied Physics Letters*, vol. 86, No. 12, (Mar. 17, 2005), 3 pgs.

Federici, John F., et al., "THz imaging and sensing for security applications—explosives, weapons and drugs", *Semiconductor Science and Technology*, vol. 20, No. 7, (Jul. 1, 2005), S266-S280.

Ito, Hiroshi, et al., "Continuous THz-wave generation using antenna-integrated uni-travelling-carrier photodiodes", *Semiconductor Science and Technology*, vol. 20, No. 7, (Jul. 1, 2005), S191-S198.

Ito, Hiroshi, et al., "High-Speed and High-Output InP—InGaAs Unitraveling-Carrier Photodiodes", *IEEE Journal of Selected Topics in Quantum Electronics*, vol. 10, No. 4, (Jul. 1, 2004), 709-727.

Ito, Hiroshi, et al., "Photonic Generation of Continuous THz Wave Using Uni-Traveling-Carrier Photodiode", *Journal of Lightwave Technology*, vol. 23, No. 12, (Dec. 2005), 4016-4021.

Matsuura, Shuji, et al., "Generation of CW Terahertz Radiation with Photomixing", *Terahertz Optoelectronics (Topics in Applied Physics*, vol. 97), (2005), 157-202.

Sartorius, B., et al., "Telecom Components for Terahertz Applications: LT InGaAs Photoconductors for Coherent Detection Close the Gap", *ECOC 2007*, (Sep. 16, 2007), 2 pgs.

Sartorius, B., "Terahertz Transmitters and Receivers", *OFC/NFOEC 2008*, (Feb. 24, 2008), 1691-1693.

Schomburg, E., et al., "InGaAs/InAlAs superlattice detector for THz radiation", *Physica E*, vol. 13, (2002), 912-915.

Siegel, Peter H., et al., "Antennas for Terahertz Applications", *2006 IEEE Antennas and Propagation Society International Symposium*, (2006), 2383-2386.

Suzuki, Masato, et al., "Fe-Implanted InGaAs photoconductive terahertz detectors triggered by 1.56 um femtosecond optical pulses", *Applied Physics Letters*, vol. 86, No. 16, (Apr. 15, 2005), 3 pgs.

Tani, Masahiko, et al., "Detection of terahertz radiation with low-temperature-grown GaAs-based photoconductive antenna using 1.55 um probe", *Applied Physics Letters*, vol. 77, No. 9, (Aug. 28, 2000), 1396-1398.

Tonouchi, Masayoshi, "Cutting-edge terahertz technology", *Nature Photonics*, vol. 1, (Feb. 2007), 97-105.

Wilk, Rafal, et al., "THz Time-Domain Spectrometer Based on LT-InGaAs Photoconductive Antennas Exited by a 1.55 um Fibre Laser", *2007 Conference on Lasers and Electro-Optics IEEE*, (May 5, 2007), 1033-1034.

* cited by examiner

METHOD FOR CREATING AND COHERENTLY DETECTING TERAHERTZ RADIATION

PRIORITY CLAIM TO RELATED APPLICATIONS

This application is a national stage application under 35 U.S.C. §371 of PCT/EP2008/007840, filed Sep. 12, 2008, and published as WO 2009/036984 A1 on Mar. 26, 2009, which claims priority to German Application No. 10 2007 044 839.4, filed Sep. 14, 2007, which applications and publication are incorporated herein by reference and made a part hereof in their entirety, and the benefit of priority is claimed thereto.

The invention relates to a device for producing and coherently detecting terahertz radiation, according to the preamble of the main claim, as well as to a use of such a device.

Terahertz radiation is suitable for material examination, since this radiation on the one hand penetrates through materials such as textiles, paper or plastics, in an unhindered manner, but on the other hand also has no ionisation effect, which is harmful for some applications. Thus electromagnetic radiation in the terahertz range (THz range) is suitable in particular for medical examinations and for screening with safety examinations.

In order to detect radiation produced by strong terahertz transmitters only detectors for incoherent power measurements, such as golay cells, are known in the state of the art. In contrast to this, a coherent detection of produced terahertz radiation is advantageous, since it may detect even the smallest of signals with a significantly higher sensitivity and thus permits more accurate material examinations in a significantly shorter time. For this, generic devices are known, which comprise a laser light source as well as a transmitter antenna which may be activated by way of a laser light source, for producing terahertz radiation, and a receiver with a receiver antenna which may be activated by the same laser light source. With such a device according to the state of the art, a photo-conductive antenna serves as a receiver antenna, wherein the transmitter antenna with regard to construction is designed just as the photo-conductive receiver antenna of the receiver, from which it differs merely by way of the fact that a bias voltage is applied to electrodes of the transmitter antenna, on account of which the desired terahertz radiation is produced given an activation of the transmitter antenna. By way of such a symmetric construction, one succeeds in the terahertz radiation coming from the transmitter antenna being able to be coherently detected by the photo-conductive receiver antenna of the receiver, when this is activated by the same laser light source.

A disadvantage of this state of the art results due to the fact that in the outlined manner, only relatively weak terahertz radiation may be produced with photo-conductor transmitter antennae, which places undesired limits on the use of a respective device for screening strong samples and at large distances.

This document describes the coherent detection of terahertz radiation that can be combined with a relatively powerful production of terahertz radiation and thus may be universally applied. In an example, such a device can be used for examining a sample.

According to an example of the invention, this can be achieved by a device with the features of the main claim. Advantageous designs and further developments can be deduced, such as from the features of the dependent claims.

Advantageously, a comparatively powerful terahertz radiation may be produced without for this reason having to make do without the coherent detection of this terahertz radiation, such as by way of the fact that the transmitter antenna, with an example of the invention presented here, can comprise a photo-diode as a light-sensitive element, that the receiver antenna as a photo-sensitive element can comprise a photo-conductor and that both are sensitive to laser light of the same wavelength.

The invention is rendered possible due to the insight, that against expectations, it is not necessary to design the transmitter antenna and an antenna of the receiver in a similar manner and thus use a symmetrical construction, for the coherent detection of a terahertz radiation which is produced by way of a transmitter antenna activated by way of a laser light source. Transmitter antennae for a production of terahertz radiation which comprise a photo-diode as a light-sensitive element are not suitable for the mixing of terahertz radiation and the optical signal which is required for coherent receiving, due to the very different current-voltage characteristics which are different in the forward direction and blocking direction. For this reason, due to a symmetrical construction, the state of the art limited itself to using exclusively photo-conductive antennae for the transmitter antenna, inasmuch as a coherent detection was provided. In order to render such transmitter antennae adequately rapid for a production of terahertz radiation, until now one was reliant on ensuring a very rapid recombination of light-induced charge carriers by way of a large number of defects in a photoconductive element of the transmitter antenna, which in turn resulted in a very low efficiency of the photo-effect and of the light terahertz conversion. In contrast, with the photo-diode for the transmitter antenna which is described here, an adequately high speed may be achieved without any problem by way of the use of suitably thinner layers, without for this having to accept a lower efficiency of the photo-effect and the light terahertz conversion. Thereby, an asymmetrical construction results with an example of the present invention, with which the transmitter antenna is designed with a photo-diode as a light-sensitive element, whereas a photo-conductive antenna is applied for the coherent receiver.

With typical designs of the invention, the photo-diode of the transmitter antenna is contacted with at least two antenna conductors, which may be designed for example as strip conductors on a substrate. This substrate, under certain circumstances, may also serve as a substrate for the photo-diode. A comparatively high radiation power of the produced terahertz radiation may be achieved by way of the photo-diode being subjected to a bias voltage in a blocking direction. With regard to the photo-diode, it may for example be the case of a UTC (uni-travelling-carrier) photo-diode. Such photo-diodes which are particularly suitable due to a particularly rapid activation ability, are known per se, see for example the publication in Semiconductor Science and Technology, 20 (2005), pages 191 to 198.

Since the photo-conductive antenna of the receiver, and the transmitter antenna are to be activated by the same laser light source for the purpose of the coherent detection, both are to be designed such that the photo-diode and a light-sensitive region of the photo-conductive receiver antenna are light-sensitive to light of the same wavelength.

With preferred designs of the invention, this corresponds to the wavelength region of 1 µm to 2 µm, particularly preferably of 1 µm to 1.6 µm, in which very rapid photo-diodes and a developed technology is available from telecom developments. The present standard photo-conductor for terahertz applications in contrast are based on GaAs and for activation require a wavelength which is shorter-waved than 850 nm For this reason, in the mentioned case for the coherent receivers, one requires photo-conductors from other materials, with a sensitivity in the spectral region of 1 μm to 2 μm.

With advantageous designs of the invention, in particular for the wavelength region 1 μm to 1.6 μm, the receiver antenna has a photo-conductor, with which at least one photo-conductive layer is arranged between in each case two adjacent semiconductor boundary layers, wherein the semiconductor boundary layers have a larger band gap and a higher defect density than the at least one photo-conductive layer. Thereby, the device should be designed such that the laser light source may radiate into the photo-conductive layer or the photo-conductive layers in an as unhindered as possible manner. Advantageously, by way of this construction of the photo-conductive receiver antenna, one succeeds in the photo-conductor one the one hand having an adequately low dark conductivity, but thereby on the other hand being quick enough to permit a detection of the terahertz radiation with an activation by way of laser light, which is also suitable for a production of the terahertz radiation with a photo-diode. The latter specifically demands the use of lasers with comparatively long wavelengths (>1 μm), with which one is confronted with the difficulty of the respective photo-conductors having too long a recombination time or too high a dark conductivity, in order to be suitable for photo-conductive antenna. If on the other hand the photo-conductive layer or each of the photo-conductive layers is arranged in each case between two adjacent semiconductor boundary layers of the described type, then one may achieve the adequately low dark conductivity by way of relatively few defects being provided in the photo-conductive layer or in the photo-conductive layers, whereas an adequately rapid removal of light-induced charge carriers is effected by way of a capture in the adjacent semiconductor boundary layers. Thereby, one may achieve particularly good results if the at least one photo-conductive layer has a layer thickness of less than 30 nm. In order to obtain a photo-conductive receiver antenna, which is suitable for the coherent detection of terahertz radiation with the transmitter antenna based on a photo-diode, the photo-conductive layer may be manufactured on the basis of an InGaAs semiconductor material or an InGaAsP semiconductor material. Thereby, a doping of the photo-conductive layer with beryllium lends itself. The semiconductor boundary layers may on the other hand be manufactured of InAlAs or material containing InAlAs, with which the desired characteristics may be realised.

In the preferred spectral region of 1 μm to 2 μm, in particular fibre-pulse lasers are suitable as a laser light source, and these are characterised by way of an activation ability for very short pulses as well as by a compact construction shape and a simple coupling of the emission in glass fibres, One may envisage the laser light source being connected in each case by way of a glass fibre, to the transmitter antenna and the photo-conductive receiver antenna. By way of this, one may succeed in light produced by the laser light source being led onto the photo-diode as well as onto the light-sensitive region of the photo-conductive receiver antenna, with a comparatively simple construction.

A device for changing the time-of-flight may be provided between the laser light source and the photo-conductive receiver antenna and/or between the laser light source and the transmitter antenna, so that the transmitter antenna and the photo-conductive antenna of the receiver may be matched to one another such the photo-conductive receiver antenna is activated in a temporally correlated manner with the transmitter antenna, such that a coherent detection is possible.

One advantageous application of the device of the described type for examining a sample with terahertz radiation envisages the sample being arranged between the transmitter antenna and the photo-conductive receiver antenna, and the transmitter antenna and the photo-conductive receiver antenna being activated with coherent radiation of the laser light source. Then a receiver signal for different delays of the time-of-flight may be detected by way of a device for changing a time-of-flight between the laser light source and the photo-conductive receiver antenna or between the laser light source and the transmitter antenna, wherein this detection permits a scanning of a signal course of the terahertz radiation. The mixed signal between the terahertz signal and the laser signal, which is obtained by way of variation of the time-of-flight in the temporal interval, may be converted by way of Fourier transformation into a terahertz spectrum, from which in turn one may derive the terahertz characteristics of a sample.

In one embodiment of the invention, the laser light source may be set up for producing light pulses, for example for producing light pulses of a pulse length of between 10 femtoseconds (fs) and 10 picoseconds (ps). By way of a suitable activation of the transmitter antenna, one may produce a terahertz pulse in a simple manner with such pulse lengths.

One alternative envisages the laser light source comprising two lasers which produce radiation superimposing on one another and which are off-tuned with respect to one another, for producing an optical beat. A beat frequency thereby results, which corresponds to a difference of the frequencies of the two lasers. If the superimposed radiation of the two lasers is directed onto the photo-diode, then the transmitter antenna may produce a terahertz radiation with a frequency corresponding to the beat frequency. For this, the two layers are preferably off-tuned to one another by a frequency difference of between 0.1 terahertz and 10 terahertz. One preferred embodiment of the invention envisages at least one of the two lasers being tuneable, so that in this manner one may set the beat frequency. A measurement, for example an examination of a sample, may be advantageously carried out with radiation of different frequencies by way of this. A tuning of at least one of the lasers may thereby be carried out by way of temperature control thus by way of heating or cooling the laser, or by way of electronic tuning.

In particular in the case of a laser light source with two lasers for producing radiation superimposing on one another, one may envisage a beam delay element with a controllable refractive index being integrated into a beam path of the laser light source. With this, one may achieve a delay of the time-of-flight with an advantageously shock-insensitive construction, compared to conventional devices for changing a time-of-flight, which comprise mechanically adjustable mirrors. The beam delay element may thereby for example be designed as a semiconductor with a refractive index which is dependent on current or voltage. If the laser light source comprises two lasers in the described manner, the beam delay element with the controllable refractive index may thereby be integrated into beam path of one of the two lasers. A comparatively low delay of the radiation coming from this laser, by a phase of the light wave, then results in an absolute shift path of the terahertz beat which is a multiple larger, likewise by a phase. This may already be sufficient for scanning the course of a receiver signal for examining a sample. One may thus avoid expensive mechanical elements with displaceable minors. Of course, with regard to an as symmetrical as possible construction of the laser light source, one may also integrate two suitable beam delay elements into the beam path of in each case of the two lasers.

Figure 2:
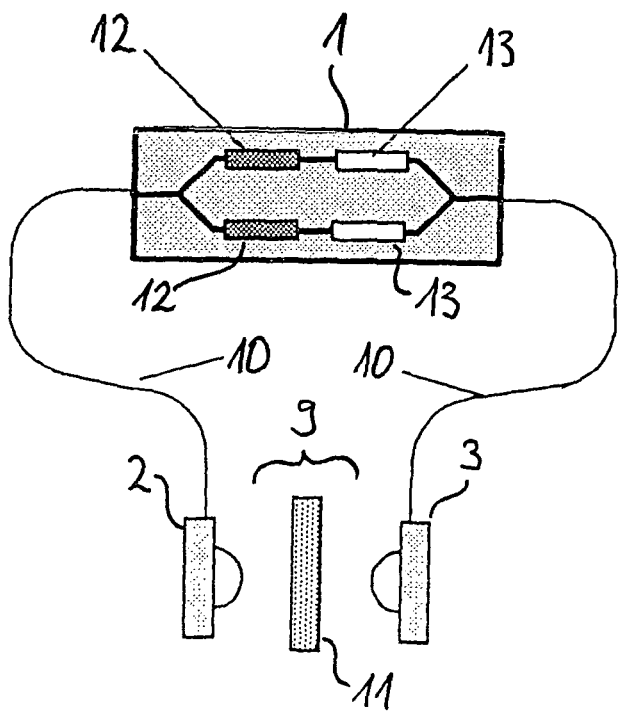
Figure 3:
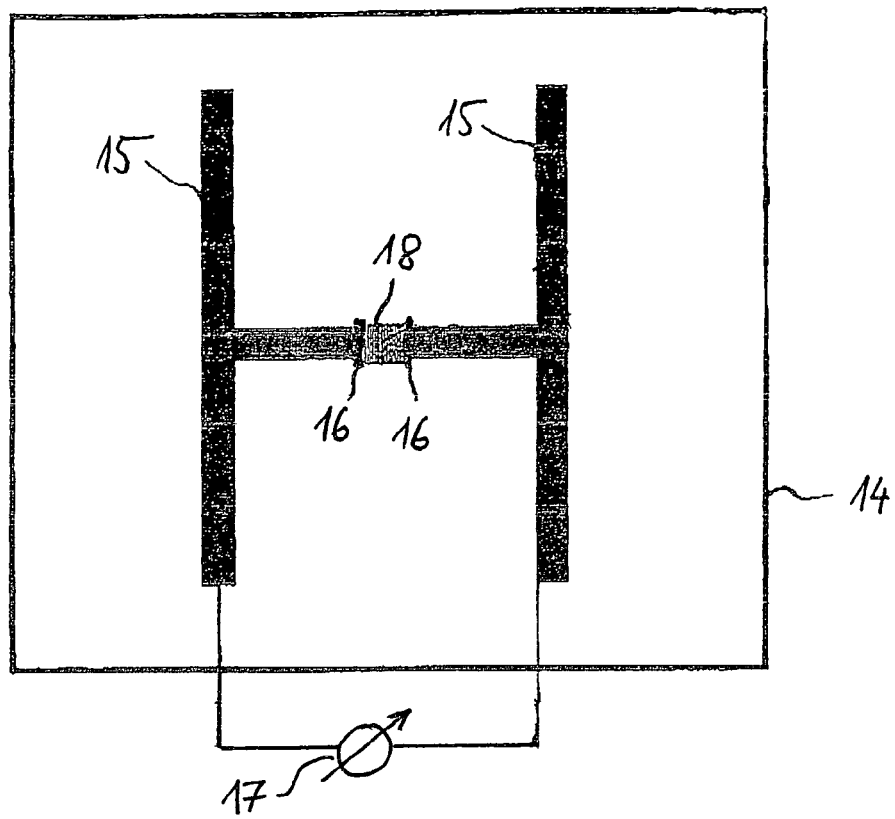
Figure 4:
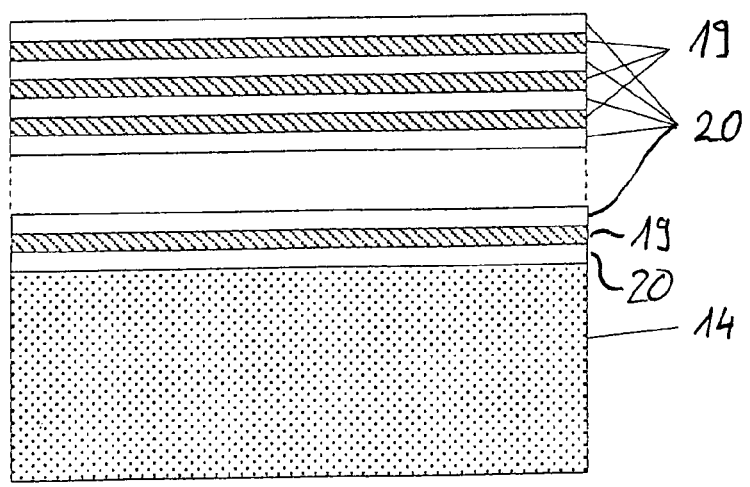

Embodiment examples of the invention are hereinafter described by way of the FIGS. 1 to 4. There are shown in:

FIG. 1 a schematic representation of one device in one embodiment of the invention, FIG. 2 likewise in a schematic representation, another embodiment of the invention, FIG. 3 a plan view of a photo-conductive receiver antenna of the devices of FIGS. 1 and 2 and FIG. 4 a cross section through a light-sensitive region of the photo-conductive receiver antenna of FIG. 3.

A device for producing and coherently detecting terahertz radiation is represented in FIG. 1, which comprises a laser light source 1, a transmitter antenna 2 which may be activated by way of the laser light source, for producing terahertz radiation, and a receiver with a photoactive receiver antenna 3 which may be activated by the same laser light source 1. Laser radiation coming from the laser light source 1 is divided by way of a beam splitter 4 and with the help of several minors 5 is led onto a light-sensitive region of the photo-conductive receiver antenna 3 as well as onto the transmitter antenna 2. Thereby, a device 6 for changing a time-of-flight, which for this purpose comprises moving minors 7, is provided between the laser light source 1 and the photo-conductive receiver antenna 3. The laser radiation may in each case be led as a free beam between the laser light source 1, the minors 5, the device 6 and the photo-conductive receiver antenna 3 or the transmitter antenna 2, or however with the help of glass fibres which in turn may render a few or all of the mirrors 5 superfluous.

The transmitter antenna 2 comprises a photo-diode as a light-sensitive element, which is contacted by two antenna conductors, wherein the antenna conductors are designed as strip conductors on a substrate which also carries the photo-diode. With regard to the photo-diode, it is the case of a UTC photo-diode, which together with the antenna conductors forms a terahertz transmitter antenna of the type shown in the article "Continuous THz-wave generation using antenna-integrated uni-travelling-carrier photo-diodes" by Hiroshi Ito et al. (see semiconductor Science and Technology Vol. 20, year 2005, pages 191 to 198). This photo-diode is subjected to a bias voltage in a blocking direction, due to which, with the impingement of the laser radiation produced by the laser light source 1, a flow of current arises, which in turn causes a terahertz radiation coming from the transmitter antenna 2. The photo-diode operates with a wavelength of 1.55 µm, wherein the light-sensitive region of the photo-conductive receiver antenna 3 becomes conductive when hit by light of the same wavelength. The laser light source 1 is selected such that the laser radiation coming from it has a wavelength of 1.55 µm and is thus suitable for activating the transmitter antenna 2 as well as the photo-conductive receiver antenna 3. For this, the laser light source 1 has a fibre-pulse laser, which is suitable for producing light pulses of a length between 10 fs and 10 ps. An activation of the transmitter antenna with such light pulses leads to a production of short terahertz pulses by the transmitter antenna 2, which in turn may be coherently detected with the photo-conductive receiver antenna 3 which is simultaneously activated by the laser radiation.

The photo-conductive receiver antenna 3 is described in yet more detail further below. Reflectors 8 are arranged between the photo-conductive receiver antenna 3 and the transmitter antenna 2, with which reflectors the terahertz radiation is led from the transmitter antenna 2 through a test space 9 to the photo-conductive receiver antenna 3.

In order to examine a sample, this may be arranged in the test space 9 between the transmitter antenna 2 and the photo-conductive receiver antenna 3, and the transmitter antenna 2 and the photo-conductive receiver antenna 3 may be simultaneously activated with coherent radiation of the laser light source 1. A receiver signal may thereby be detected for different delays of a time-of-flight between the laser light source 1 and the photo-conductive receiver antenna 3 by way of a displacement of the movable minors 7, and thus a terahertz signal arising at the photo-conductive receiver antenna 3 may be scanned. The measurement variable obtained in the time range is converted by way of a Fourier transformation into a spectrum, and one may deduce material characteristics of the sample from this.

Of course, the device 6 may alternatively be arranged between the beam splitter 4 and the transmitter antenna 2 and accordingly one may vary a time-of-flight between the laser light source 1 and the transmitter antenna 2.

One modification of the device shown in FIG. 1 envisages the laser light source 1 comprising two lasers, which are slightly off-tuned to one another, wherein radiation departing from these lasers is superimposed for producing an optical beat. Thereby, the two lasers may for example be off-tuned to one another by a frequency difference of between 0.1 THz and 10 THz, which leads to the production of a continuous terahertz radiation of a suitable frequency by way of the transmitter antenna 2. Additionally, then at least one of the two lasers of the laser light source 1 may be designed in a tuneable manner, so that the frequency difference and, with a frequency of the beat which corresponds to this frequency difference, the frequency of the produced terahertz radiation may also be varied.

Another design of a comparable device for the production and coherent detection of terahertz radiation is represented in FIG. 2. Recurring features there are again provided with the same reference numerals. Here, the laser light source 1 is connected in each case by way of a flexible glass fibre 10 to the transmitter antenna 2 as well as to the photo-conductive receiver antenna 3. Also shown by way of example in FIG. 2 is a sample 11, which is introduced into the test space 9 between the transmitter antennas 2 and the photo-conductive receiver antenna 3.

The transmitter antenna 2 and the photo-conductive receiver antenna 3 are designed as with the previously described embodiment example. The laser light source 1 on the other hand here comprises two DFB lasers 12 which are arranged in a common InP-chip, of which at least one may be tuneable for example by way of a temperature control of the respective DFB laser 12. The emissions of the two DFB lasers 12 are superimposed for producing a beat, and the superimposed signal is led to two outcoupling surfaces, wherein radiation exiting at one of these outcoupling surfaces is led to the transmitter antenna 2, and radiation exiting at the other outcoupling surface is led to the photo-conductive receiver antenna 3. In each case, a beam delay element 13 with a controllable refractive index is arranged in the beam path of the two DFB lasers 12, between the DFB lasers 12 and the photo-conductive receiver antenna 3, on the mentioned InP-chip. A time-of-flight between the DFB lasers 12 and the photo-conductive receiver antenna 3 may be varied at least slightly with these beam delay elements 13. The radiation departing from the DFB lasers 12 serves as a carrier wave for a beat produced on superimposing this radiation. A delay of the radiation of one of these DFB lasers 12 by a phase of the carrier wave thereby leads to a displacement of a produced beat signal by exactly the same phase, which however scales with the wavelength of the terahertz radiation, which is a multiple larger. A scanning of the terahertz signal arriving at the photo-conductive receiver antenna 3 in the manner already described, may therefore be achieved with the present embodiment by way of a comparatively slight delay of the radiation of one of the two DFB lasers 12, said delay achievable in a high-frequency manner with electrical means. Of course, the beam delay elements 13 which have a current-dependent or voltage-dependent refractive index, instead of this, may also be arranged between the DFB lasers 12 and the transmitter antenna 2.

By way of the use of the photo-diode as a light sensitive element of the transmitter antenna 2, the terahertz radiation produced for examining the sample 11 may be produced with a comparatively high radiation power, since the high reaction speed of the transmitter antenna 2 to short light pulses or high-frequency modulated light, which is required for this, may be achieved by way of suitably thin layers within the photo-diode. In contrast, a rapid recombination of light-induced charge carriers would become necessary with a use of a photo-conductive antenna also for producing terahertz radiation known from the state of the art, which in turn would result in a very low radiation power.

On examination of the sample 11 with the device shown in FIG. 2, a receiver signal may be detected with the photo-conductive receiver antenna 3, in an advantageous manner for different relative phase positions of the radiation departing from the DFB lasers 12 for activating the photo-conductive receiver antenna 3, in order by way of the beat signal which shifts therewith, to scan the terahertz signal arriving at the photo-conductive receiver antenna 3.

A plan view of the photo-conductive receiver antenna 3 may be recognised in FIG. 3. Two strip conductors 15 are arranged on a carrier 14 of this photo-conductive receiver antenna 3, said strip conductors serving as antenna conductors and being connected to two electrodes which lie opposite one another. Moreover, the strip conductors 15 are contacted with a sensor 17 for detecting detected signals. The photo-conductive receiver antenna 3, in at least one a light-sensitive region 18 between the electrodes 16, comprises a layer structure which may be recognised in FIG. 4. There, in the present example, about 100 photo-conductive layers 19 are arranged on the substrate 14, which in turn are arranged in each case between two adjacent semiconductor boundary layers 20. A few layers in the drawing have been omitted in the drawing for the purpose of a better overview. The photo-conductive layers 19 in each case have a layer thickness of about 12 nm and are manufactured of an InGaAs semiconductor material doped with beryllium or an InGaAsP semiconductor material. The semiconductor boundary layers 20 in contrast are manufactured of InAlAs and have a layer thickness of about 8 nm. The semiconductor boundary layers 20 thereby are designed such that they have a large band gap and higher defect density, thus a higher density of defects, than the photo-conductive layers 19. Thus a photo-conductor is realised in the light-sensitive region 18, said photo-conductor being characterised by a very low dark conductivity, by a high reaction speed and by a light sensitivity in the region of a wavelength of 1.55 μm. The devices of FIGS. 1 and 2 are in each case designed such that the laser light source 1 beams into the photo-conductive layers 19 of this photo-conductor.

The light-sensitive region 18 thus becomes conducting when laser radiation which comes from the laser light source 1 hits it. If simultaneously a terahertz signal of the terahertz radiation departing from the transmitter antenna 2 arrives at the photo-conductive receiver antenna 3, charge carriers produced by way of the laser radiation are set into motion in the light-sensitive region 18, which is why in turn a corresponding electrical signal may be detected with the sensor 17. Thus a coherent detection of the terahertz radiation produced with the transmitter antenna 2 is possible, although the respective device has an asymmetrical construction with a transmitter antenna 2 based on a photo-diode on the one hand, and with a photo-conductive antenna for the receiver on the other hand.

Thus concluding, what is put forward is a device for producing and coherently detecting terahertz radiation comprising a laser light source, a transmitter antenna which may be activated by way of the laser light source, for producing terahertz radiation, and a receiver with a photo-conductive receiver antenna which may be activated by the same laser light source, wherein the emitter antenna comprises a photo-diode as a light-sensitive element, whilst the receiver antenna in a light-sensitive region comprises a photo-conductor as a light-sensitive element, which is as light sensitive as the photo-diode to laser light of an equal wavelength.

The invention claimed is:

1. A device for producing and coherently detecting terahertz radiation, comprising a laser light source, a transmitter antenna capable of being activated by way of the laser light source, for producing the terahertz radiation as a continuous terahertz radiation, and a receiver with a receiver antenna capable of being activated by the same laser light source, the transmitter antenna and the receiver antenna being activated with coherent radiation of the laser light source such that the receiver antenna is activated in a temporally correlated manner with the transmitter antenna, such that coherent detection is possible,
    wherein the laser light source comprises two lasers, a first laser of the two lasers producing a first radiation output off-tuned and superimposed on a second radiation output of the second laser of the two lasers, the first radiation output and the second radiation output producing an optical beat, a frequency of the continuous terahertz radiation corresponding to a beat frequency of the optical beat,
    wherein the transmitter antenna comprises a light-sensitive element that comprises a photo-diode, and the receiver antenna comprises a light-sensitive element that comprises a rapid photo-conductor,
    wherein the photo-diode and the photo-conductor are photo-sensitive in a common wavelength region, the photo-conductor including a photo-conductive layer containing InGaAs semiconductor material or InGaAsP semiconductor material such that the common wavelength region lies within a wavelength interval of 1 μm to 2 μm, the photo-conductor having a low dark conductivity and detecting the terahertz radiation with an activation triggered by the optical beat produced by the laser light source comprising two lasers.

2. The device according to claim 1, wherein the photo-diode of the transmitter antenna is capable of being contacted with at least two antenna conductors.

3. The device according to claim 1, wherein the photo-diode is configured to be subjected to a bias voltage in a blocking direction.

4. The device according to claim 1, wherein the photo-diode comprises a UTC photo-diode.

5. The device according to claim 1, wherein the photo-conductor of the receiver antenna comprises at least one photo-conductive layer arranged between two adjacent semiconductor boundary layers, wherein the semiconductor boundary layers have a larger band gap and a higher defect density than the at least one photo-conductive layer.

6. The device according to claim 5, wherein the at least one photo-conductive layer has a layer thickness of less than 30 nm.

7. The device according to claim 5, wherein the semiconductor boundary layers contain an InAlAs semiconductor material.

8. The device according to claim 1, wherein the laser light source is suitable for producing radiation of a wavelength of between 1 μm and 2 μm.

9. The device according to claim 1, wherein the laser light source is connected to the photo-diode of the transmitter antenna and to the photo-conductor of the receiver antenna, in each case by way of a flexible glass fibre.

10. The device according to claim 1, wherein a device for changing the time-of-flight is provided between the laser light source and the receiver antenna and/or between the laser light source and the transmitter antenna.

11. The device according to claim 1, wherein the two lasers are off-tuned to one another by between 0.1 THz and 10 THz.

12. The device according to claim 1, wherein at least one of the two lasers is tuneable.

13. The device according to claim 1, wherein a beam delay element with a controllable refractive index is integrated into a beam path of at least one of the two lasers.

14. The device according to claim 1, configured for examining a sample with terahertz radiation, wherein the sample is arranged between the transmitter antenna and the receiver antenna, and the transmitter antenna and the receiver antenna are concurrently activated with coherent radiation of the laser light source.

15. The device according to claim 14, wherein a receiver signal for different delays of a time-of-flight between the laser light source and the receiver antenna or the transmitter antenna is detected.

* * * * *